United States Patent
Awad et al.

(10) Patent No.: US 10,188,116 B1
(45) Date of Patent: Jan. 29, 2019

(54) METHOD OF SYNTHESIZING *DOUM* NANOPARTICLES

(71) Applicant: KING SAUD UNIVERSITY, Riyadh (SA)

(72) Inventors: Manal Ahmed Gasmelseed Awad, Riyadh (SA); Awatif Ahmed Hendi, Riyadh (SA); Khalid Mustafa Osman Ortashi, Riyadh (SA); Hany Mohamed Yehia, Cairo (EG); Mohamed Mahmoud Hafez Ahmed, Cairo (EG); Hatem Salama Mohamed Ali, Cairo (EG); Mohamed Fekry Serag El-Din, Minuyfiya (EG); Zeinab Korany Mohamed Hassan, Cairo (EG)

(73) Assignee: King Saud University, Riyadh (SA)

( * ) Notice: Subject to any disclaimer, the term of this patent is extended or adjusted under 35 U.S.C. 154(b) by 0 days.

(21) Appl. No.: 15/855,332

(22) Filed: Dec. 27, 2017

(51) Int. Cl.
*A61K 36/889* (2006.01)
*A01N 65/40* (2009.01)
*A01N 25/12* (2006.01)

(52) U.S. Cl.
CPC ............. *A01N 65/40* (2013.01); *A01N 25/12* (2013.01)

(58) Field of Classification Search
None
See application file for complete search history.

(56) References Cited

U.S. PATENT DOCUMENTS 9,623,067 B1    4/2017    Awad et al.

FOREIGN PATENT DOCUMENTS

| KR | 1020040110242 A | 5/2004 |
| KR | 1020150082734 A | 7/2015 |
| WO | 2016076691 A2 | 5/2016 |

OTHER PUBLICATIONS

Angellier et al. (2004) 5, 1545-1551. (Year: 2004).*
Seleem et al. (2015) Food and Nutrition Sciences, vol. 06, Issue 07, pp. 622-632. (Year: 2015).*
Aboshora et al. (2016) J. Food Sci. Technol. 53(1): 591-600. (Year: 2016).*
Aboshora et al. (2014) Tropical Journal of Pharmaceutical Research, Dec. 2014, 13(12): 2057-2063. (Year: 2014).*
Le Corre et al. (2010) Biomacromolecules, 11, 1139-1153. (Year: 2010).*
Aboshora, "Effect of Extraction Method and Solvent Power on Polyphenol and Flavonoid Levels in *Hyphaene thebaica* L Mart (Arecaceae) (Doum) Fruit, and its Antioxidant and Antibacterial Activities," Tropical Journal of Pharmaceutical Research, Dec. 2014.
Aamer, "Characteristics of aqueous doum fruit extract and its utilization in some novel products," Annals of Agricultural Sciences, vol. 61, Issue 1 Jun. 2016, pp. 25-33.

* cited by examiner

*Primary Examiner* — Christopher R Tate
*Assistant Examiner* — Russell G Fiebig
(74) *Attorney, Agent, or Firm* — Richard C. Litman

(57) ABSTRACT

Doum nanoparticles can be synthesized by drying Doum fruit, reducing the dried Doum fruit to a powder or flour, and subjecting the powder to acid hydrolysis or alcohol hydrolysis to provide Doum nanoparticles. The Doum nanoparticles can be used as a food preservative. When compared to bulk Doum particles, the Doum nanoparticles can provide substantially increased antibacterial activity.

1 Claim, 2 Drawing Sheets

METHOD OF SYNTHESIZING *DOUM* NANOPARTICLES

BACKGROUND

1. Field

The disclosure of the present patent application relates to nanoparticle synthesis, and particularly, to synthesis of Doum nanoparticles.

2. Description of the Related Art

Nanoparticles exhibit completely new or improved properties compared to their corresponding bulk materials. Nanoparticles can provide, for example, increased catalytic property, increased efficacy, and/or decreased toxicity compared to the corresponding bulk materials. Nanoparticles also possess a very high surface to volume ratio. As such, they are particularly useful in applications where high surface areas are critical for success.

Nanoparticles can be synthesized from chemical or natural products. Nanoparticle synthesis from natural products is generally more preferable. When compared to nanoparticles manufactured from chemicals, for example, nanoparticles made from natural products are more eco-friendly, readily available, cost effective, and have little, if any, side effects.

*Hyphaene thebaica* (Doum fruit) is a desert palm native to Egypt, Sudan, Sub-Saharan Africa, and Western India. Doum fruit is a good source of essential minerals, such as potassium, sodium, calcium, magnesium, and phosphorus. Doum fruit also includes B-complex, vitamins, carbohydrates, and fiber, which are essential for good nutrition. The aqueous extract of Doum fruit has demonstrated antioxidant and anticancer activities.

SUMMARY

Doum nanoparticles can be synthesized by drying Doum fruit, reducing the dried Doum fruit to a powder or flour, and subjecting the dried fruit powder to alcohol or acid hydrolysis to provide Doum nanoparticles. For the alcohol or acid hydrolysis, the dried fruit powder can be mixed with ethanol or sulfuric acid solution, for example. The Doum nanoparticles are safe for human consumption and can be useful as a food preservative. When compared to bulk Doum particles, the Doum nanoparticles can provide substantially increased antibacterial activity.

These and other features of the present disclosure will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1A:
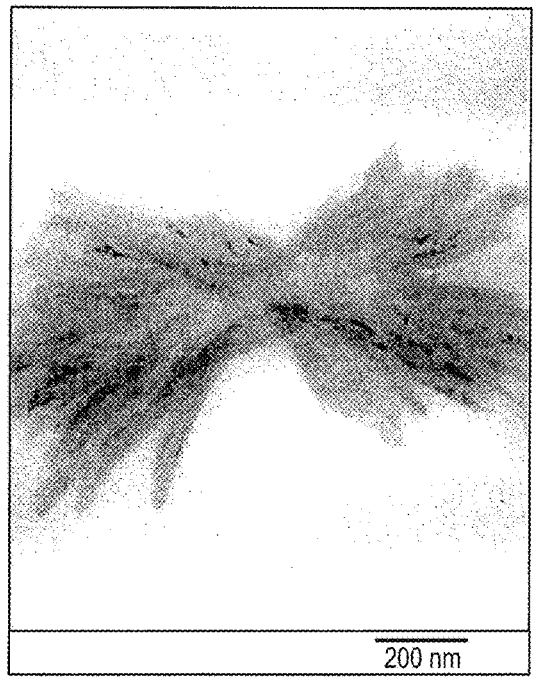
FIGS. 1A and 1B are TEM images of a Doum nanoparticle.
Figure 1B:
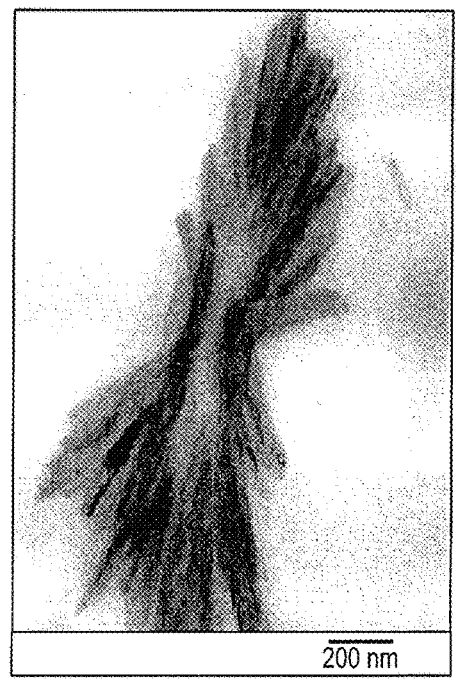
Figure 2:
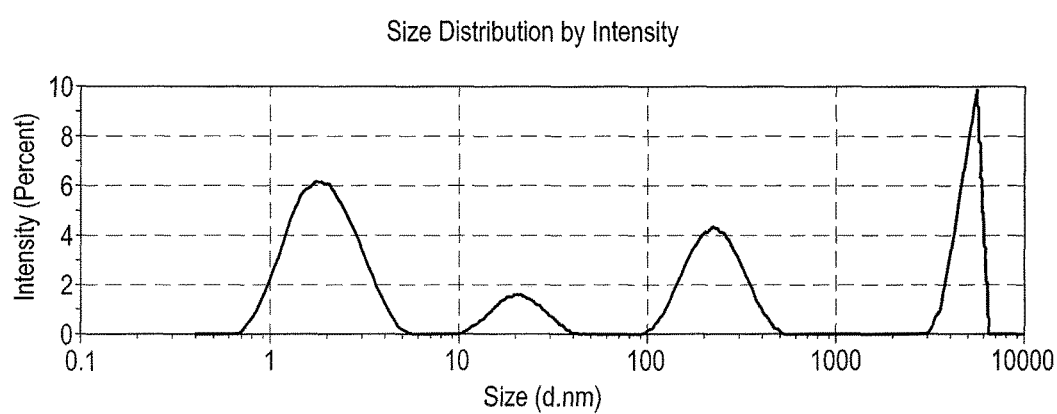
FIG. 2 is a graph showing the particle size distribution of the Doum nanoparticles.

Doum nanoparticles can be synthesized by drying Doum fruit, reducing the dried fruit to a powder or flour, and subjecting the powder to hydrolysis, e.g. alcohol hydrolysis or acid hydrolysis. The alcohol hydrolysis can include mixing the dried fruit powder with an alcohol, e.g., ethanol, to provide a mixture. The acid hydrolysis can include mixing the dried fruit powder with an acid solution, e.g., sulfuric acid solution, to provide a mixture. Distilled water can be added to the mixture to provide the Doum nanoparticles. For example, about 150 grams of the dried fruit powder can be mixed with about 60 mL to about 100 mL ethanol solution. Alternatively, about 5 grams of the dried fruit powder can be mixed with about 3.16 M of sulfuric acid solution. The Doum nanoparticles can have a particle size of about 220 nm or less. FIGS. 1A and 1B are TEM images of the Doum nanoparticles. FIG. 2 is a graph showing the particle size distribution of the Doum nanoparticles.

The Doum nanoparticles can be used as a food preservative. As described in detail herein, when compared to bulk Doum particles, the Doum nanoparticles can provide substantially increased antibacterial activity (Table 2). The Doum nanoparticles are non-toxic and safe for human consumption.

The present inventors found that Doum nanoparticles have more increased total phenols, total flavonoids, and antioxidant activity compared to normal Doum extract. Table 1 compares pf total Phenols, total Flavonoids, DPPH (2,2-diphenyl-1-picrylhydrazyl) radical scavenging activity, ABTS (2,4,6-Tri(2-Pyridyl)-s-triazine) radical scavenging activity and Ferric reducing antioxidant power (FRAP) of normal Doum extract and Doum nanoparticles, prepared as described in Example 1.

TABLE 1

|  | T. Phenols (mg Gallic acid/g sample) M ± SD | T. Flavonoids (mg Catachin/g sample) M ± SD | T. Flavonoids (mg Rutin/g sample) M ± SD | DPPH (%) M ± SD | ABTS (mmol Trolox/g sample) M ± SD | FRAB (mmol Trolox/g sample) M ± SD |
|---|---|---|---|---|---|---|
| Doum extract | 108.328 ± 0.239 | 1.600 ± 0.038 | 17.101 ± 0.419 | 93.71 ± 0.339 | 10.448 ± 0.225 | 5.018 ± 0.026 |
| Doum nano particles (Example 1) | 137.152 ± 0.640 | 3.325 ± 0.024 | 33.211 ± 0.264 | 94.95 ± 0.480 | 133.337 ± 1.197 | 10.333 ± 0.097 |

Values are means of three replicates.
Results were given as mean ± SD.

The present inventors have found that Doum nanoparticles provide antioxidant activity. Table 2 compares pf total phenols, total flavonoids, DPPH (2,2-diphenlyl-1-picrylhydrazyl) radical scavenging activity, ABTS (2,4,6-Tri(2-Pyridyl)-s-triazine) radical scavenging activity and Ferric reducing antioxidant power (FRAP) of normal Doum extract and Doum nanoparticles prepared as described in Example 2.

TABLE 2

|  | T. Phenols (mg Gallic acid/g sample) M ± SD | T. Flavonoids (mg Catachin/ g sample) M ± SD | T. Flavonoids (mg Rutin/g sample) M ± SD | DPPH (%) M ± SD | ABTS (mmol Trolox/g sample) M ± SD | FRAB (mmol Trolox/g sample) M ± SD |
|---|---|---|---|---|---|---|
| Doum nanoparticles | 40.045 ± 0.558 | 0.696 ± 0.004 | 7.518 ± 0.046 | 45.01 ± 1.917 | 0.852 ± 0.050 | 1.302 ± 0.004 |
| Doum Extract (Example 2) | 108.328 ± 0.239 | 1.600 ± 0.038 | 17.101 ± 0.419 | 93.71 ± 0.339 | 10.448 ± 0.225 | 5.018 ± 0.026 |

Values are means of three replicates.
Results were given as mean ± SD.

The present teachings are further illustrated by the following examples.

Example 1

Preparation of Doum Nanoparticles and Normal Doum Extract

For preparing the Doum nanoparticles, Doum fruit was collected in March 2017 from a local market in Ed Daein City, Sudan. The seeds were removed from the Doum fruit and the fruit was sun dried for one week. The dried Doum fruit was broken into several pieces by grinding in a heavy-duty grinder to pass 1-2 mm screens to produce Doum flour or Doum powder.

To synthesize Doum nanoparticles, about 150 mg of Doum powder was dissolved in about 25 ml to about 50 ml of ethanol. The Doum ethanol solution was sprayed into about 60 mL to about 100 mL boiling distilled water dropwise with a flow rate of 0.2 ml/min in five minutes under ultrasonic conditions, with an ultrasonic power of 100 W and a frequency of 30-60 kHZ for 25-30 minutes. The solution was stirred for 15-30 minutes at about 30° C.-50° C.

The Doum flour or powder was subjected to acid hydrolysis according to the procedure of Angellier et al. Briefly, 5 g of Doum was disposed in a 100 mL flask and mixed with 3.16 M sulphuric acid solution. The flask was kept under stirring. Distilled water was then added to the flask. The Doum nanoparticles formed in the flask were filtered through a Millipore filter having a pore size of 220 nm.

Normal Doum extract was prepared by washing Doum fruits with tap water and drying the washed fruits in an oven at 50° C. for 24 hours. The external crust (epicarp) of the Doum fruits was crushed using a grinder machine (Mockmill 200 Stone Grain Mill by Wolfgang Mock). The crushed portion was soaked in water (100 mg/ml) for 24 hours in a refrigerator at 5° C., then tested on the microorganisms listed in Table 3. As shown in Table 3 and described below, the bacterial strains were not affected by the normal Doum extract.

Example 3

Effect of Doum Nanoparticles on Bacteria

Agar diffusion method was used to determine the antimicrobial activity of Doum nanoparticles and normal Doum extract against foodborne and contaminated bacteria listed in Table 2. One hundred microliters of $10^6$/ml of each active bacterial strain (grown on brain Heart Infusion agar (Oxoid CM 1136) for 24 h at 37° C.) were spread on the surface of Muller Hinton agar plates (Oxoid CM 0337). The active bacterial strains are listed in Table 2 below. 100 mg/ml of Doum nanoparticles and the normal Doum extract (without Doum nanoparticles) prepared as described in Example 1 were dissolved in sterilized water and left overnight in the refrigerator. Then, three holes were formed on the agar by using a sterile cork borer with a diameter of 6 mm. The first hole received a 50 µL volume of a Doum nanoparticle solution (Dn). The second hole received a 50 µL volume of the normal Doum extract dissolved in water (D). The third hole received a 50 µL volume of only water (C). Then, the agar plates were incubated at 37° C. for 24 h. Zone of inhibition was measured for every strain tested. The results are provided in Table 2 below.

TABLE 3

Effect of Doum nanoparticles and normal Doum extracts on bacterial strains as zone of inhibition (mm)

|  | Zone of inhibition (mm) | |
|---|---|---|
| Bacterial strains | Doum nanoparticles extract | Normal Doum extract (without nanoparticles) |
| Bacillus cereus ATCC 14579 | 20 | — |
| Bacillus subtilis subsp. spizizenii ATCC 6633 | 15 | — |
| Bacillus subtilis (Local isolte) | 20 | — |
| Staph. aureus ATCC 29737 | 18 | — |
| Klebsiella pneumoniae ATCC 10031 | 12 | — |
| Proteus sp. (local isolate) | 12 | — |
| Psedomonas aeruginosa ATCC 25619 | 15 | — |
| Escherichia coli ATCC 11775 | 18 | — |
| Serratia marcescens (local isolte) | 17 | — |
| Salmonella typhimurium | 12 | — |
| Ratio of activity (%) | 100 | 0 |

As shown in Table 3, all bacterial strains were affected by Doum nanoparticles, but not by the normal Doum extract (without nanoparticles). The zone of inhibition of the Doum nanoparticles ranged from about 12 mm to about 20 mm. Generally, the effect of Doum nanoparticles on gram positive bacteria was better than the effect on gram negative bacteria and the ratio of effect reaches to 100%. This may be due to the difference in the chemical structure of the cell wall. These results suggest that the Doum nanoparticles can be used effectively as a food preservative, thereby obviating a need to add chemical or synthetic preservatives to food.

It is to be understood that the antibacterial Doum nanoparticles and method of making same is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A method for synthesizing Doum nanoparticles for enhanced antibacterial activity, comprising:
    drying Doum fruit to provide a dried fruit;
    reducing the dried fruit to a powder;
    subjecting the powder to alcohol hydrolysis to provide the Doum nanoparticles, wherein the alcohol hydrolysis comprises mixing the powder with ethanol under ultrasonic conditions of 30-60 kHZ for 25-30 minutes to provide a mixture and adding distilled water to the mixture to create a solution;
    stirring the solution for 15-30 minutes at a temperature of 30-50° C.; and
    filtering the solution to obtain the Doum nanoparticles, wherein the Doum nanoparticles have a particle size of 220 nm.

* * * * *